(12) United States Patent
Higuchi et al.

(10) Patent No.: US 9,151,768 B2
(45) Date of Patent: Oct. 6, 2015

(54) METHOD FOR QUANTIFYING THE AMOUNT OF CHOLESTEROL IN HIGH-DENSITY LIPOPROTEIN 3

(75) Inventors: Maiko Higuchi, Gosen (JP); Yasuki Itoh, Gosen (JP)

(73) Assignee: DENKA SEIKEN CO., LTD., Tokyo (JP)

( * ) Notice: Subject to any disclaimer, the term of this patent is extended or adjusted under 35 U.S.C. 154(b) by 0 days.

(21) Appl. No.: 13/811,569

(22) PCT Filed: Jul. 22, 2011

(86) PCT No.: PCT/JP2011/066691
§ 371 (c)(1),
(2), (4) Date: Mar. 4, 2013

(87) PCT Pub. No.: WO2012/011563
PCT Pub. Date: Jan. 26, 2012

(65) Prior Publication Data
US 2013/0164769 A1    Jun. 27, 2013

(30) Foreign Application Priority Data
Jul. 23, 2010    (JP) ................................ 2010-166395

(51) Int. Cl.
*C12Q 1/60*    (2006.01)
*G01N 33/92*    (2006.01)

(52) U.S. Cl.
CPC . *G01N 33/92* (2013.01); *C12Q 1/60* (2013.01)

(58) Field of Classification Search
None
See application file for complete search history.

(56) References Cited

U.S. PATENT DOCUMENTS

| 6,194,164 | B1 | 2/2001 | Matsui et al. |
| 2005/0037504 | A1 | 2/2005 | DiMagno et al. |
| 2009/0188812 | A1* | 7/2009 | Broughall et al. ......... 205/777.5 |
| 2009/0203054 | A1* | 8/2009 | Murphy et al. ................ 435/11 |

FOREIGN PATENT DOCUMENTS

| JP | 2001-346598 A | 12/2001 |
| JP | 2009-207463 A | 9/2009 |
| WO | 98/47005 A1 | 10/1998 |

OTHER PUBLICATIONS

Okada et al., J. Clin. Lab. Anal., 15:223-229 (2001).*
Chaiyasat et al., Colloid Polym. Sci. 285:557-562 (2007).*
International Search Report issued in PCT/JP2011/066691 mailed Oct. 18, 2011.

(Continued)

*Primary Examiner* — Blaine Lankford
*Assistant Examiner* — Thomas J Visone
(74) *Attorney, Agent, or Firm* — Birch, Stewart, Kolasch & Birch, LLP

(57) ABSTRACT

A method that enables quantification of cholesterol in high-density lipoprotein 3 (HDL3) in a test sample without requiring a laborious operation is disclosed. The method for quantifying cholesterol in HDL3 comprises reacting, with a test sample, a surfactant that specifically reacts with high-density lipoprotein 3, and quantifying cholesterol. The method enables specific quantification of HDL3 cholesterol in a test sample using an automatic analyzer without requirement of a laborious operation such as ultracentrifugation or pretreatment. Further, quantification of the HDL2 cholesterol level can also be carried out by subtracting the HDL3 cholesterol level from the total HDL cholesterol level obtained by a conventional method for quantifying the total HDL cholesterol in a test sample.

1 Claim, 1 Drawing Sheet

(56) References Cited

OTHER PUBLICATIONS

Ahmadraji, T. et al, "The evolution of selective analysis of HDL and LDL cholesterol in clinical and point of care testing," Analytical Methods, Aug. 7, 2013, vol. 5, No. 15, pp. 3612-3625.

Extended European Searhch Report for Appl. No. 11809733.6 dated Dec. 17, 2013.

Ito, Y. et al, "Development of a homogeneous assay for measurement of high-density lipoprotein-subclass cholesterol," Clinica Chimica ACTA, Sep. 19, 2013, vol. 427, pp. 86-93.

Matsuura, F., "High Density Lipoprotein (HDL)—Role of HDL in Defense Mechanism Against Arteriosclerosis," Igaku No Ayumi, Jun. 30, 2007, vol. 221, No. 13, pp. 1074-1080 (w/ English Abstract).

* cited by examiner

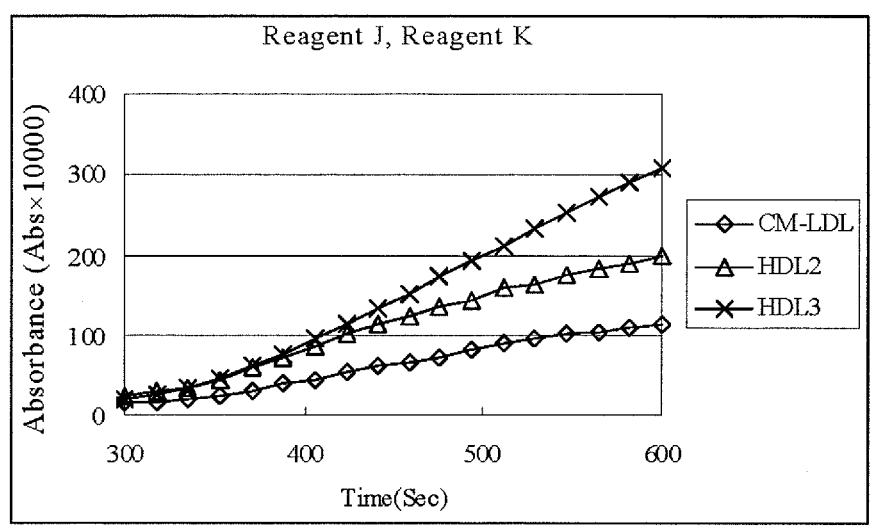

METHOD FOR QUANTIFYING THE AMOUNT OF CHOLESTEROL IN HIGH-DENSITY LIPOPROTEIN 3

TECHNICAL FIELD

The present invention relates to a method for quantifying cholesterol in high-density lipoprotein 3 (which may be hereinafter referred to as "HDL3") (cholesterol in HDL3 may be hereinafter referred to as "HDL3 cholesterol").

BACKGROUND ART

Since high-density lipoprotein (HDL) receives cholesterol from various tissues including walls of blood vessels with arteriosclerosis, it is involved in the action of removal of cholesterol accumulated in cells. Therefore, HDL cholesterol is also called the reverse cholesterol transport system. High-density lipoprotein is known to have a negative correlation with arteriosclerotic diseases such as coronary arteriosclerosis. Accordingly, an HDL value lower than a predetermined lower limit is regarded as an indication of dyslipidemia, and the value is known to be useful as an index of arteriosclerosis.

HDL is constituted by apoprotein, phospholipid, cholesterol and triglyceride. HDL has a density of d=1.063 to 1.210 g/mL, and can be divided into two fractions, that is, HDL2 wherein d=1.063 to 1.125 g/mL and HDL3 wherein d=1.125 to 1.210 g/mL. A notch is found at the portion of d=1.125 in the distribution curve of lipoprotein, and the part having higher densities in the curve corresponds to HDL3. Alternatively, HDL can be divided into subfractions based on the difference in the content of apolipoprotein E among apoproteins in HDL, and HDLs having higher contents of apoE are defined as apoE-rich HDL.

In terms of the functions, HDL has been conventionally studied as a whole, but each of the subfractions HDL2 and HDL3 is now known to have unique functions. It is clinically known that CETP deficiency prevents cholesterol transport from HDL to LDL and IDL, leading to an increase in the HDL cholesterol level. The HDL increased by CETP deficiency is HDL2. HDL2 is said to have an antiarteriosclerotic action. It is also said that CETP deficiency causes an increase in apoE-rich HDL, and that, since apoE-rich HDL has a strong cholesterol-drawing ability and antiplatelet action, it is a good HDL. Further, a decrease in the hepatic lipase activity prevents conversion of HDL3 to HDL2, resulting in an increase in HDL3. It is suggested that increased HDL3 leads to increased incidence rates of coronary artery diseases. In view of such tendencies, it is expected that measurement of each HDL subfraction may contribute to judgment of whether or not a patient is suffering from an arteriosclerotic disease and of the cause of the disease. Further, at present, in view of these functions of HDL subfractions, manufacturers are developing therapeutic agents that inhibit the function of CETP, decrease the LDL cholesterol level, and increase the HDL cholesterol level.

Establishment of a simple method for measuring the HDL subfractions may lead to detailed elucidation of their functions, and to their therapeutic effects in the future.

Examples of methods for measuring HDL subfractions which have been known so far include ultracentrifugation, high-performance liquid chromatography (HPLC), HDL3 precipitation (Patent Document 1) and NMR.

In ultracentrifugation, fractionation is carried out utilizing the difference in the density of lipoprotein. This method has drawbacks in that the operation requires a skill; the method takes many days; and the cost is high. In the method by Okazaki et al. wherein HPLC is used for separating HDL2 and HDL3, the operation takes a long time, and special equipment is required. HDL3 precipitation is a method wherein a reagent containing a divalent metal ion and dextran sulfate is used to aggregate lipoproteins other than HDL3, and HDL3 in the supernatant portion is recovered by centrifugation and measured using an automatic analyzer. This method is not widely used since the method has drawbacks in that the operation of this method also requires a skill; the method is a manual method; the method requires an operation of sample pretreatment; and a certain length of time is required before measurement. Further, NMR, which is a method wherein the number of particles of lipoprotein is measured by magnetic resonance, is not commonly employed since the method requires special equipment.

There is another method for analyzing an HDL subfraction (Patent Document 2). Although this method enables measurement with a general purpose automatic analyzer, the method employs a method wherein a surfactant is used to prevent an enzyme from acting on lipoproteins other than HDL3. Therefore, since the HDL3 reaction is allowed to proceed in the presence of the lipoproteins other than the lipoprotein of interest, the measurement might be influenced by such lipoproteins or, in cases where the prevention is not sufficient, the lipoproteins other than HDL3 might be undesirably measured together.

Thus, as an alternative to the above methods, a reagent which enables simple and more selective quantification of the cholesterol level needs to be invented.

PRIOR ART DOCUMENTS

Patent Documents

[Patent Document 1] JP 2009-207463 A
[Patent Document 2] JP 2001-346598 A

SUMMARY OF THE INVENTION

Problems to be Solved by the Invention

An object of the present invention is to provide a method that enables quantification of HDL3 in a test sample without requiring a laborious operation.

Means for Solving the Problems

The present inventors intensively studied to discover surfactants that specifically react with high-density lipoprotein 3. The present inventors then inferred that HDL3 cholesterol in a test sample can be quantified by allowing such a surfactant to react with the test sample and then quantifying cholesterol. The present inventors experimentally confirmed that this is possible, thereby completing the present invention.

That is, the present invention provides a method for quantifying cholesterol in high-density lipoprotein 3, the method comprising reacting, with a test sample, a surfactant(s) that specifically react(s) with high-density lipoprotein 3, and quantifying cholesterol.

Effect of the Invention

By the present invention, HDL3 cholesterol in a test sample can be specifically quantified with an automatic analyzer without requirement of a laborious operation such as ultracentrifugation or pretreatment. Further, quantification of the HDL2 cholesterol level can also be carried out by subtracting the HDL3 cholesterol level from the total HDL cholesterol level obtained by a conventional method for quantifying the total HDL cholesterol in a test sample.

BRIEF DESCRIPTION OF THE DRAWINGS

FIG. 1 shows a diagram illustrating a result of Examples of the present invention in terms of changes in the absorbance of each fraction after addition of Reagent K.

BEST MODE FOR CARRYING OUT THE INVENTION

The test sample to be subjected to the method of the present invention is not restricted as long as HDL3 cholesterol in the sample can be quantified, and the test sample is preferably serum or blood plasma, or a dilution thereof. Serum or a dilution thereof is especially preferred.

In the method of the present invention, a test sample is reacted with a surfactant that specifically reacts with HDL3 (surfactant that hardly reacts with lipoproteins other than HDL3). Examples of the surfactant that specifically reacts with HDL3 include nonionic surfactants such as polyoxyethylene distyrene-modified phenyl ether, polyoxyethylene lauryl ether and p-isooctyl polyoxyethylene phenol formaldehyde polymers; amphoteric surfactants such as lauryl dimethyl-aminoacetic acid betaine and polyoxyethylene lauryl ether; and cationic surfactants such as fatty acid series phosphoric acid esters. Each of these surfactants may be used alone, or two or more types of the surfactants may be used in combination. Among the surfactants, polyoxyethylene lauryl ether is especially preferred.

More specific examples of the surfactant that specifically reacts with HDL3 include nonionic surfactants such as polyoxyethylene distyrene-modified phenyl ether Emulgen A90 (trade name; manufactured by Kao Corporation; company names hereinafter represent names of manufacturers, and all names described together with company names hereinafter represent trade names), polyoxyethylene lauryl ether Emulgen 120 (Kao Corporation) and p-isooctyl polyoxyethylene phenol formaldehyde polymer Triton-WR-1339 (Nacalai Tesque) and polyoxyethylene lauryl ether Persoft NK-100 (NOF Corporation); amphoteric surfactants such as lauryl dimethyl-aminoacetic acid betaine Nissan Anon BL-SF (NOF Corporation); and anionic surfactants such as fatty acid series phosphoric acid ester ADEKA COL PS-440E (ADEKA Corporation).

When the term "react" is used for a surfactant in the present invention, the term means that the surfactant leads lipoprotein to the outside of the reaction system, making an enzyme act easily, or means to protect lipoprotein such that an enzyme cannot act on the lipoprotein.

The concentration of the surfactant is preferably 0.01 to 5.0% (w/v), more preferably 0.05 to 2.0% (w/v).

In the method of the present invention, cholesterol is quantified by the reaction of the above surfactants. Methods of quantification per se of cholesterol are well known, and any of the well known methods may be used. A concrete description is also given in Examples below. For example, ester-type cholesterol in lipoprotein is hydrolyzed with cholesterol esterase to produce free cholesterol and a fatty acid, and the produced free cholesterol and free cholesterol inherently existing in lipoprotein are converted using cholesterol oxidase to generate cholestenone and hydrogen peroxide. A quinone pigment is then formed in the presence of peroxidase, and quantified. Examples of compounds that generate a quinone pigment include HDAOS (N-(2-hydroxy-3-sulfopropyl)-3,5-dimethoxyaniline), DAOS (N-ethyl-N(-2-hydroxy-3-sulfopropyl)-3,5-dimethoxyaniline sodium salt) or TOOS (N-ethyl-N(-2-hydroxy-3-sulfopropyl)-3-methylaniline sodium salt dihydrate) and 4-aminoantipyrine, but the compounds are not restricted as long as the combination allows generation of a quinone pigment. In cases where cholesterol esterase and cholesterol oxidase are used in the preceding step described later, the cholesterol esterase and cholesterol oxidase used in the preceding step may be used as they are in the step of the present invention (step of reacting an HDL3-specific surfactant), without further addition.

The concentration of the compound for generation of a quinone pigment is preferably about 0.5 to about 2.0 mmol/L in the case of HDAOS, or 0.1 to 2.0 mmol/L in the case of 4-aminoantipyrine. The concentration of peroxidase is preferably 0.4 to 5.0 U/mL. In the step of decomposing the hydrogen peroxide generated in the preceding step with catalase, a catalase inhibitor sodium azide is employed by addition to the reaction liquid in Step 2. The concentration of sodium azide in this case is usually about 0.1 g/L to about 1.0 g/L.

As the reaction liquid, various buffers used in normal biochemical reactions may be used, and the pH of the reaction liquid is preferably between 5 and 8. The solution is preferably Good's, Tris, phosphate or glycine buffer solution, and is preferably a Good's buffer such as bis(2-hydroxyethyl)iminotris(hydroxyethyl)methane(Bis-Tris), piperazine-1,4-bis(2-ethanesulfonic acid) (PIPES), piperazine-1,4-bis(2-ethanesulfonic acid) sesqui sodium salt monohydrate (PIPES 1.5Na), 3-morpholinopropanesulfonic acid (MOPSO), N,N-bis(2-hydroxyethyl)-2-aminoethanesulfonic acid (BES), 2-[4-(2-hydroxyethyl)-1-piperazinyl]ethanesulfonic acid (HEPES) or piperazine-1,4-bis(2-hydroxy-3-propanesulfonic acid) (POPSO).

The reaction temperature is preferably about 25 to about 40° C., more preferably 35 to 38° C., most preferably 37° C. The reaction time is not restricted, and is usually about 2 to about 10 minutes.

The method of the present invention can also be carried out by directly reacting the surfactant with the test sample, but is preferably carried out by first performing the preceding step for transferring cholesterol in lipoproteins other than HDL or HDL3 to the outside of the reaction system and then subjecting the sample after the preceding step to the method of the present invention, in view of more accurate quantification of HDL3 cholesterol.

The preceding step is preferably carried out in the presence of a surfactant that reacts with lipoproteins other than HDL or a surfactant that reacts with lipoproteins other than HDL3. Preferred examples of the surfactant that reacts with lipoproteins other than HDL include nonionic surfactants such as polyoxyethylene-polyoxypropylene condensates, polyoxyethylene nonylphenyl ether, amide nonion and polyoxyethylene polycyclic phenyl ether having an HLB value of 14 to 17; and anionic surfactants such as polyoxyethylene alkyl ether sodium sulfate. Each of these surfactants may be used alone, or two or more types of the surfactants may be used in combination. More specific examples of the surfactant include Pluronic, Pluronic P123 (ADEKA Corporation), Pluronic F88 (ADEKA Corporation), Levenol WX (Kao Corporation), Nonion HS-220 (NOF Corporation), Nymid MT-215 (NOF Corporation), Newcol-723 (NOF Corporation), Newcol-2614 (Nippon Nyukazai Co, Ltd.) and Newcol-714 (Nippon Nyukazai Co, Ltd.).

Examples of the surfactant that reacts with lipoproteins other than HDL3 include, but are not limited to, nonionic surfactants such as polyoxyethylene distyrene-modified phenyl ether, polyoxyethylene-polyoxypropylene condensates and polyoxyethylene-stearylamine; anionic surfactants such as, amide ether sulfate; amphoteric surfactants such as coconut oil fatty acid-amidopropyldimethyl-aminoacetic acid betaine, alkyl dimethyl-aminoacetic acid betaine and lauryl betaine; and cationic surfactants such as lauryl trimethyl ammonium chloride. More specifically, examples of the nonionic surfactants include polyoxyethylene distyrene-modified phenyl ether Emulgen A500 (trade name; manufactured by Kao Corporation; company names hereinafter represent names of manufacturers, and all names described together with company names hereinafter represent trade names); polyoxyethylene-polyoxypropylene condensates Pluronic F127 (ADEKA Corporation), Pluronic F68 (ADEKA Corporation) and Pluronic P103 (ADEKA Corporation) and polyoxyethylene-stearylamine Nymeen 5210 (NOF Corporation); examples of the anionic surfactants include amide ether sulfate Sunamide CF-10 (NOF Corporation); examples of the amphoteric surfactants include a coconut oil fatty acid-amidopropyldimethyl-aminoacetic acid betaine Nissan Anon BDF-SF (NOF Corporation), alkyl dimethyl-aminoacetic acid betaine Nissan Anon BF (NOF Corporation) and lauryl betaine Amphitol 24B (Kao Corporation); and the cationic surfactants include lauryl trimethyl ammonium chloride Kohtamin 24P (Kao Corporation). Each of these may be used alone, or two or more types of these may be used in combination.

The concentration of the surfactant to be used in the preceding step is preferably 0.01 to 5.0% by weight, more preferably about 0.03 to about 3.0% by weight.

In the preceding step, cholesterol is transferred to the outside of the reaction system by the reaction with the surfactant. The term "transferred to the outside of the reaction system" herein means that cholesterol and esters thereof are eliminated or protected such that the cholesterol and esters thereof are not involved in the later steps.

The term "elimination" herein means that cholesterol of lipoprotein in a test sample is degraded such that the cholesterol does not affect the reaction for measurement of cholesterol in a later step. Examples of the method for eliminating lipoprotein cholesterol include a method wherein cholesterol esterase and cholesterol oxidase are allowed to act on the cholesterol, followed by decomposition of the produced hydrogen peroxide into water and oxygen using catalase. Alternatively, a hydrogen donor may be reacted with the produced hydrogen peroxide using peroxidase to convert the hydrogen peroxide to a colorless quinone. The method for eliminating lipoprotein cholesterol is not restricted to these. The method of elimination of cholesterol per se is known in the art, and is also described concretely in Examples below.

The term "protection" means to protect lipoprotein in a test sample such that the lipoprotein does not react upon cholesterol measurement in a later step. Examples of the method of protection of lipoprotein include, but are not limited to, a method wherein a surfactant is used to specifically protect each lipoprotein such that cholesterol esterase and cholesterol oxidase do not act on the lipoprotein.

The present inventors further discovered that phospholipase and sphingomyelinase act on lipoproteins but hardly act on HDL3. Accordingly, by allowing phospholipase and/or sphingomyelinase (these may be hereinafter collectively referred to as the "phospholipase and/or the like") to coexist with the above-described surfactant, HDL3 cholesterol can be more accurately quantified, which is preferred.

The phospholipase is not restricted as long as it acts on phosphatidyl choline. Phospholipase A, phospholipase C and phospholipase D are preferred, and phospholipase C and phospholipase D are especially preferred. Since the phospholipase and/or the like are commercially available, commercially available products may be preferably used. Each of the phospholipase and/or the like may be used alone, or two or more types of the phospholipase and the like may be used in combination.

The final concentration of the phospholipase and/or the like (total concentration, in cases where two or more types of the phospholipase and/or the like are used—the same applies hereinafter) is preferably about 0.1 to about 100 U/mL, more preferably about 0.2 to about 50 U/mL.

Also in cases where the preceding step is carried out in the coexistence of a surfactant, the reaction conditions (reaction temperature, time, buffer and the like) are as described above.

In the preceding step, by preliminarily adding an enzyme system and a surfactant for transferring cholesterol to the outside of the reaction system at the same time, both steps can be carried out at the same time as a single step. It should be noted that the surfactant used is different between Step 1 and Step 2.

In the preceding step, in cases where cholesterol esterase and cholesterol oxidase are used, the concentration (the concentration means the final concentration unless otherwise specified in the present specification) of cholesterol esterase is preferably about 0.1 to about 10.0 U/mL, more preferably about 0.2 to about 2.0 U/mL. The concentration of cholesterol oxidase is preferably about 0.05 to about 10.0 U/mL, more preferably about 0.1 to about 1.0 U/mL. The cholesterol esterase is not restricted as long as it acts on ester-type cholesterol, and examples of the cholesterol esterase which may be used include commercially available products such as cholesterol esterase (CEBP, CEN) manufactured by Asahi Kasei Corporation and cholesterol esterase (COE-311, COE-312) manufactured by Toyobo Co., Ltd. Further, the cholesterol oxidase is not restricted as long as it acts on free cholesterol, and examples of the cholesterol oxidase which may be used include commercially available products such as cholesterol oxidase (COM) manufactured by Asahi Kasei Corporation and cholesterol oxidase (COO-311, COO-321, COO-331) manufactured by Toyobo Co., Ltd.

In the preceding step, in cases where peroxidase is used, the concentration of peroxidase is preferably about 2.0 to about 5.0 U/mL, more preferably about 3.0 to about 4.0 U/mL. In cases where a compound for conversion into a colorless quinone is used, the concentration of the compound is preferably about 0.4 to about 0.8 mmol/L.

Other conditions (reaction temperature, reaction time, buffer and the like) may be the same as those in the method of the present invention described above.

The present invention will now be described more concretely by way of Examples below. However, the present invention is not limited to the Examples below.

EXAMPLES

Reference Example 1

Reagent A and Reagent B having the compositions described below were prepared, and reagents were prepared by adding various surfactants to Reagent A to a concentration of 0.1% (w/v) or 1.0% (w/v). Immediately before the measurement, Reagent A containing the various surfactants described below was mixed with Reagent B at a ratio of 1:3. Cholesterol in each of the HDL2 fraction and the HDL3 fraction was reacted with the resulting mixture, and the final absorbances at a main wavelength of 700 nm and a sub-wavelength of 600 nm were measured and compared.

Fractionation was carried out to obtain the HDL2 fraction and the HDL3 fraction as follows. A test sample containing HDL, that is, serum was subjected to ultracentrifugation using a solution with sodium chloride and sodium bromide such that separation occurs at a density at the border between HDL2 and HDL3 (1.125), and each resulting fraction was recovered.

Table 1 below shows surfactants with which the ratio of HDL2/HDL3 was not more than 0.75 and the ratios of CM-IDL/HDL3 and LDL/HDL3 were not more than 0.75. These surfactants were determined to be surfactants that react with HDL3. Table 2 shows surfactants with which the ratio of HDL2/HDL3 was not less than 1.25 and the ratios of CM-IDL/HDL2 and LDL/HDL2 were not less than 1.25. These surfactants were determined to be surfactants that react with lipoproteins other than HDL3. Table 3 shows surfactants with which the ratio of HDL2/HDL3 was between 0.75 and 1.25 and the ratios of CM-IDL/HDL2, LDL/HDL2, CM-IDL/HDL3 and LDL/HDL3 were not more than 0.75. These surfactants were determined to be surfactants that react with HDL. Table 4 shows surfactants with which the ratio of HDL2/HDL3 was between 0.75 and 1.25 and the ratios of CM-IDL/HDL2, LDL/HDL2, CM-IDL/HDL3 and LDL/HDL3 were not less than 0.75. These surfactants were determined to be surfactants that react with all lipoproteins. Table 5 shows surfactants that could not be grouped into any of the above categories. These surfactants were determined to be surfactants that react with lipoproteins other than HDL.

Reagent A

| | |
|---|---|
| BES buffer (pH 7.0) | 100 mmol/L |
| HDAOS | 0.7 mmol/L |
| Catalase | 600 U/L |
| Cholesterol oxidase | 1.4 U/mL |
| Cholesterol esterase | 0.8 U/mL |

Reagent B

| | |
|---|---|
| BES buffer (pH 6.6) | 100 mmol/L |
| Sodium azide | 0.1% |
| 4-Aminoantipyrine | 4.0 mmol/L |
| Peroxidase | 2.4 U/mL |

TABLE 1

| | Concentration | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Emulgen A90 | 1% | 219 | 161 | 339 | 448 | 0.76 | 0.65 | 0.49 | 0.47 | 0.36 |
| | 0.1% | 198 | 119 | 306 | 519 | 0.59 | 0.65 | 0.38 | 0.39 | 0.23 |
| Emulgen 120 | 1% | 560 | 564 | 806 | 1267 | 0.64 | 0.69 | 0.44 | 0.70 | 0.45 |
| | 0.1% | 494 | 465 | 499 | 793 | 0.63 | 0.99 | 0.62 | 0.93 | 0.59 |
| Nissan Anon BL-SF | 1% | 441 | 941 | 721 | 1244 | 0.58 | 0.61 | 0.35 | 1.31 | 0.76 |
| | 0.1% | 396 | 290 | 321 | 294 | 1.09 | 1.23 | 1.35 | 0.90 | 0.99 |
| Triton WR-1339 | 1% | 317 | 216 | 560 | 972 | 0.58 | 0.57 | 0.33 | 0.39 | 0.22 |
| | 0.1% | 203 | 117 | 385 | 582 | 0.66 | 0.53 | 0.35 | 0.30 | 0.20 |
| Persoft NK-100 | 1% | 687 | 603 | 1036 | 1569 | 0.66 | 0.66 | 0.44 | 0.58 | 0.38 |
| | 0.1% | 503 | 421 | 648 | 785 | 0.83 | 0.78 | 0.64 | 0.65 | 0.54 |
| Adekatol PS-440E | 1% | 771 | 1099 | 1124 | 1633 | 0.69 | 0.69 | 0.47 | 0.98 | 0.67 |
| | 0.1% | 1019 | 1410 | 1555 | 1715 | 0.91 | 0.66 | 0.59 | 0.91 | 0.82 |

(Unit: Abs × 10000)

Emulgen A90, Emulgen 120, Nissan Anon BL-SF, Triton WR-1339, Persoft NK-100 and Adekatol PS-440E were surfactants that specifically react with HDL3.

TABLE 2

| | Concentration | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Emulgen A500 | 1% | 27 | 77 | 105 | 86 | 1.22 | 0.26 | 0.31 | 0.73 | 0.90 |
| | 0.1% | 105 | 44 | 36 | 20 | 1.80 | 2.92 | 5.25 | 1.22 | 2.20 |
| Nissan Anon BDF-SF | 1% | 304 | 226 | 328 | 242 | 1.36 | 0.93 | 1.26 | 0.69 | 0.93 |
| | 0.1% | 272 | 91 | 82 | 42 | 1.95 | 3.32 | 6.48 | 1.11 | 2.17 |
| Nissan Anon BF | 1% | 512 | 461 | 581 | 571 | 1.02 | 0.88 | 0.90 | 0.79 | 0.81 |
| | 0.1% | 687 | 127 | 394 | 280 | 1.41 | 1.74 | 2.45 | 0.32 | 0.45 |
| Nymeen S210 | 1% | 485 | 252 | 290 | 222 | 1.31 | 1.67 | 2.18 | 0.87 | 1.14 |
| | 0.1% | 514 | 278 | 271 | 199 | 1.36 | 1.90 | 2.58 | 1.03 | 1.40 |
| Pluronic P103 | 1% | 87 | 72 | 102 | 81 | 1.26 | 0.85 | 1.07 | 0.71 | 0.89 |
| | 0.1% | 63 | 46 | 36 | 25 | 1.44 | 1.75 | 2.52 | 1.28 | 1.84 |
| Kohtamin 24P | 1% | 495 | 185 | 359 | 288 | 1.25 | 1.38 | 1.72 | 0.52 | 0.64 |
| | 0.1% | 580 | 323 | 307 | 177 | 1.73 | 1.89 | 3.28 | 1.05 | 1.82 |
| Sunamide CF-10 | 1% | 427 | 322 | 339 | 251 | 1.35 | 1.26 | 1.70 | 0.95 | 1.28 |
| | 0.1% | 479 | 321 | 308 | 184 | 1.67 | 1.56 | 2.60 | 1.04 | 1.74 |
| Amphitol 24B | 1% | 471 | 392 | 509 | 481 | 1.06 | 0.93 | 0.98 | 0.77 | 0.81 |
| | 0.1% | 596 | 558 | 384 | 283 | 1.36 | 1.55 | 2.11 | 1.45 | 1.97 |
| Pluronic F68 | 1% | 127 | 47 | 45 | 62 | 0.73 | 2.82 | 2.05 | 1.04 | 0.76 |
| | 0.1% | 1328 | 275 | 175 | 129 | 1.36 | 7.59 | 10.29 | 1.57 | 2.13 |
| Pluronic F127 | 1% | 523 | 260 | 138 | 109 | 1.27 | 3.79 | 4.80 | 1.88 | 2.39 |
| | 0.1% | 137 | 78 | 59 | 60 | 0.98 | 2.32 | 2.28 | 1.32 | 1.30 |

(Unit: Abs × 10000)

Emulgen A500, Nissan Anon BDF-SF, Nissan Anon BF, Nymeen S210, Pluronic P103, Kohtamin 24P, Sunamide CF-10, Amphitol 24B, Pluronic F68 and Pluronic F127 were surfactants that specifically react with lipoproteins other than HDL3.

TABLE 3

| | | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Emulgen B66 | 1% | 375 | 281 | 1434 | 1473 | 0.97 | 0.26 | 0.25 | 0.20 | 0.19 |
| | 0.1% | 361 | 185 | 1396 | 1441 | 0.97 | 0.26 | 0.25 | 0.13 | 0.13 |
| Emulgen A60 | 1% | 375 | 281 | 1434 | 1473 | 0.97 | 0.26 | 0.25 | 0.20 | 0.19 |
| | 0.1% | 361 | 185 | 1396 | 1441 | 0.97 | 0.26 | 0.25 | 0.13 | 0.13 |
| Emulgen LS110 | 1% | 851 | 1267 | 1454 | 1463 | 0.99 | 0.59 | 0.58 | 0.87 | 0.87 |
| | 0.1% | 744 | 1034 | 1518 | 1529 | 0.99 | 0.49 | 0.49 | 0.68 | 0.68 |
| Newcol-610 | 1% | 500 | 447 | 1386 | 1470 | 0.94 | 0.36 | 0.34 | 0.32 | 0.30 |
| | 0.1% | 439 | 320 | 1431 | 1472 | 0.97 | 0.31 | 0.30 | 0.22 | 0.22 |
| Newcol-2609 | 1% | 636 | 553 | 1509 | 1556 | 0.97 | 0.42 | 0.41 | 0.37 | 0.36 |
| | 0.1% | 547 | 543 | 1512 | 1502 | 1.01 | 0.36 | 0.36 | 0.36 | 0.36 |
| Newcol-CMP-11 | 1% | 681 | 519 | 1498 | 1551 | 0.97 | 0.45 | 0.44 | 0.35 | 0.33 |
| | 0.1% | 542 | 371 | 1435 | 1529 | 0.94 | 0.38 | 0.35 | 0.26 | 0.24 |
| Nissan Anon GLM-R-LV | 1% | 593 | 841 | 1219 | 1214 | 1.00 | 0.49 | 0.49 | 0.69 | 0.69 |
| | 0.1% | 92 | 112 | 68 | 59 | 1.15 | 1.35 | 1.56 | 1.65 | 1.90 |
| Newcol-710 | 1% | 506 | 491 | 1303 | 1597 | 0.82 | 0.39 | 0.32 | 0.38 | 0.31 |
| | 0.1% | 400 | 297 | 1344 | 1476 | 0.91 | 0.30 | 0.27 | 0.22 | 0.20 |

(Unit: Abs × 10000)

Emulgen B66, Emulgen A60, Emulgen LS110, Nowcol-610, Newcol-2609, Newcol-CMP-11, Nissan Anon GLM-RLV and Newcol-710 were surfactants that specifically react with HDL.

TABLE 4

| | | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Emulgen 108 | 1% | 2284 | 2390 | 2197 | 2202 | 1.00 | 1.04 | 1.04 | 1.09 | 1.09 |
| | 0.1% | 1609 | 1815 | 1585 | 1548 | 1.02 | 1.02 | 1.04 | 1.15 | 1.17 |
| Emulgen 707 | 1% | 3169 | 3021 | 2928 | 3048 | 0.96 | 1.08 | 1.04 | 1.03 | 0.99 |
| | 0.1% | 1186 | 1546 | 1443 | 1375 | 1.05 | 0.82 | 0.86 | 1.07 | 1.12 |

TABLE 4-continued

| | | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Newcol-707 | 1% | 2349 | 2700 | 2783 | 2703 | 1.03 | 0.84 | 0.87 | 0.97 | 1.00 |
| | 0.1% | 4106 | 4766 | 4850 | 4910 | 0.99 | 0.85 | 0.84 | 0.98 | 0.97 |
| Adekatol LB83 | 1% | 1592 | 1611 | 1523 | 1509 | 1.01 | 1.05 | 1.06 | 1.06 | 1.07 |
| | 0.1% | 1661 | 1680 | 1611 | 1598 | 1.01 | 1.03 | 1.04 | 1.04 | 1.05 |
| Adekatol LB103 | 1% | 1418 | 1556 | 1533 | 1492 | 1.03 | 0.92 | 0.95 | 1.02 | 1.04 |
| | 0.1% | 1228 | 1579 | 1582 | 1540 | 1.03 | 0.78 | 0.80 | 1.00 | 1.03 |
| Emulgen 909 | 1% | 4248 | 3432 | 3488 | 3407 | 1.02 | 1.22 | 1.25 | 0.98 | 1.01 |
| | 0.1% | 2467 | 2607 | 2704 | 2633 | 1.03 | 0.91 | 0.94 | 0.96 | 0.99 |

(Unit: Abs × 10000)

Emulgen 108, Emulgen 707, Newcol 707, Adekatol LB83, Adekatol LB103 and Emulgen 909 were surfactants that specifically react with all lipoproteins.

TABLE 5

| | | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Newcol-714 | 1% | 178 | 139 | 260 | 218 | 1.19 | 0.68 | 0.82 | 0.53 | 0.64 |
| | 0.1% | 203 | 116 | 220 | 203 | 1.08 | 0.92 | 1.00 | 0.53 | 0.57 |
| Newcol-723 | 1% | 127 | 96 | 178 | 135 | 1.32 | 0.71 | 0.94 | 0.54 | 0.71 |
| | 0.1% | 28 | 64 | 78 | 63 | 1.24 | 0.36 | 0.44 | 0.82 | 1.02 |
| Newcol-2614 | 1% | 137 | 111 | 211 | 177 | 1.19 | 0.65 | 0.77 | 0.53 | 0.63 |
| | 0.1% | 142 | 84 | 143 | 103 | 1.39 | 0.99 | 1.38 | 0.59 | 0.82 |
| Nymeen S215 | 1% | 207 | 169 | 226 | 170 | 1.33 | 0.92 | 1.22 | 0.75 | 0.99 |
| | 0.1% | 183 | 166 | 213 | 165 | 1.29 | 0.86 | 1.11 | 0.78 | 1.01 |
| Pluronic P123 | 1% | 187 | 142 | 222 | 169 | 1.31 | 0.84 | 1.11 | 0.64 | 0.84 |
| | 0.1% | 79 | 68 | 108 | 97 | 1.11 | 0.73 | 0.81 | 0.63 | 0.70 |
| Levenol WX | 1% | 122 | 120 | 163 | 134 | 1.22 | 0.75 | 0.91 | 0.74 | 0.90 |
| | 0.1% | 80 | 75 | 67 | 27 | 2.48 | 1.19 | 2.96 | 1.12 | 2.78 |
| Nymid MT-215 | 1% | 31 | 250 | 272 | 203 | 1.34 | 0.11 | 0.15 | 0.92 | 1.23 |
| | 0.1% | 27 | 228 | 263 | 195 | 1.35 | 0.10 | 0.14 | 0.87 | 1.17 |
| Nonion HS220 | 1% | 329 | 268 | 322 | 253 | 1.27 | 1.02 | 1.30 | 0.83 | 1.06 |
| | 0.1% | 223 | 182 | 280 | 224 | 1.25 | 0.80 | 1.00 | 0.65 | 0.81 |
| Pluronic F88 | 1% | 54 | 45 | 33 | 46 | 0.72 | 1.64 | 1.17 | 1.36 | 0.98 |
| | 0.1% | 45 | 51 | 31 | 49 | 0.63 | 1.45 | 0.92 | 1.65 | 1.04 |

(Unit: Abs × 10000)

Newcol-714, Newcol-723, Newcol-2614, Nymeen S215, Pluronic P123, Levenol WX, Nymid MT-215, Nonion HS220 and Pluronic F88 were surfactants that specifically react with lipoproteins other than HDL.

Example 1

Fractionation by ultracentrifugation was carried out to obtain the CM-LDL fraction, HDL2 fraction and HDL3 fraction, and each fraction was reacted with Reagent J described below. Reagent K described below was further added to the reaction solution to perform measurement. In the measurement, 150 µL of Reagent J was added to 2 µL of serum, and the reaction was allowed to proceed for 5 minutes with warming, followed by addition of Reagent K to the reaction solution and additional 5 minutes of reaction with warming The absorbances at a main wavelength of 700 nm and a sub-wavelength of 600 nm were measured.

Reagent J

| BES buffer (pH 7.0) | 100 mmol/L |
|---|---|
| HDAOS | 0.7 mmol/L |
| Pluronic P103 | 0.03 w/v % |
| Catalase | 600 U/L |
| Cholesterol oxidase | 1.4 U/mL |
| Cholesterol esterase | 0.8 U/mL |
| Phospholipase D | 5.0 U/mL |

Reagent K

| BES buffer (pH 6.6) | 100 mmol/L |
|---|---|
| Sodium azide | 0.1% |
| Emulgen 120 | 1.0% |
| 4-Aminoantipyrine | 4.0 mmol/L |
| Peroxidase | 2.4 U/mL |

FIG. 1 shows the result in terms of changes with time in the absorbance of each fraction after addition of Reagent K. Specific reaction with HDL3 can be seen.

The invention claimed is:

1. A method for quantifying cholesterol in high-density lipoprotein 3, said method comprising:
   reacting, with a test sample, a surfactant(s) that specifically react(s) with high density-lipoprotein 3, and quantifying cholesterol,
   wherein said surfactant is:
   at least one nonionic surfactant of p-isooctyl polyoxyethylene phenol formaldehyde polymers;
   lauryl dimethyl-aminoacetic acid betaine; and/or
   at least one anionic surfactant of fatty acid series phosphoric acid esters.

* * * * *